United States Patent
Eaton et al.

(10) Patent No.: US 9,649,331 B2
(45) Date of Patent: May 16, 2017

(54) SPRAYABLE POLYMERS AS ADHESION BARRIERS

(75) Inventors: Donald J. Eaton, Los Altos, CA (US); Bin Huang, Pleasanton, CA (US); Michael A. Savitt, River Hills, WI (US)

(73) Assignee: Ara Medical LLC, Los Altos, CA (US)

( * ) Notice: Subject to any disclaimer, the term of this patent is extended or adjusted under 35 U.S.C. 154(b) by 663 days.

(21) Appl. No.: 12/705,436

(22) Filed: Feb. 12, 2010

(65) Prior Publication Data
US 2011/0052712 A1 Mar. 3, 2011

Related U.S. Application Data

(60) Provisional application No. 61/237,669, filed on Aug. 27, 2009.

(51) Int. Cl.
| | | |
|---|---|---|
| *A61K 31/765* | (2006.01) | |
| *A61K 9/14* | (2006.01) | |
| *A61P 41/00* | (2006.01) | |
| *A61K 9/00* | (2006.01) | |
| *A61K 9/12* | (2006.01) | |
| *A61K 47/32* | (2006.01) | |
| *A61K 47/36* | (2006.01) | |

(52) U.S. Cl.
CPC .......... *A61K 31/765* (2013.01); *A61K 9/0014* (2013.01); *A61K 9/12* (2013.01); *A61K 47/32* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 5,626,863 A | * | 5/1997 | Hubbell et al. ............... 424/426 |
| 5,906,997 A | | 5/1999 | Schwartz et al. |
| 6,017,301 A | | 1/2000 | Schwartz et al. |
| 6,034,140 A | | 3/2000 | Schwartz et al. |

(Continued)

FOREIGN PATENT DOCUMENTS

| | | | |
|---|---|---|---|
| DE | 39 16 020 | 11/1990 | |
| EP | 0927053 | * 4/2003 | ............. A61L 27/00 |

(Continued)

OTHER PUBLICATIONS

Wu, X. S.; Wang, N. Journal of Biomaterial Science Polymer Edition, 2001, v. 12, iss. 1, p. 21-34.*

(Continued)

*Primary Examiner* — Mina Haghighatian
*Assistant Examiner* — Erin Hirt
(74) *Attorney, Agent, or Firm* — Squire Patton Boggs (US) LLP

(57) ABSTRACT

A formulation for generating an adhesion barrier that includes a plurality of particles or a dry powder that is made of a polymer combination of at least one biodegradable polymer and at least one water soluble polymer is disclosed. Methods of making and delivering the formulation are further disclosed. The formulation of particles is deposited on a surface of internal body tissue and the deposited formulation absorbs moisture from the tissue and forms a film over the surface. The film acts as an adhesion barrier by reducing or preventing adhesion of the surface to other body tissue.

6 Claims, 10 Drawing Sheets

(56) References Cited

U.S. PATENT DOCUMENTS

Figure 1A:
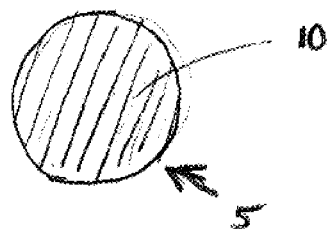
Figure 1B:
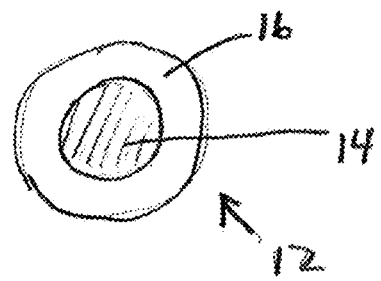

| | | | |
|---|---|---|---|
| 6,136,333 A * | 10/2000 | Cohn et al. | 424/423 |
| 6,153,212 A | 11/2000 | Mao et al. | |
| 6,566,245 B2 | 5/2003 | Deas et al. | |
| 6,869,938 B1 | 3/2005 | Schwartz et al. | |
| 7,182,957 B2 | 2/2007 | Zentner et al. | |
| 7,202,281 B2 * | 4/2007 | Cohn et al. | 514/772.1 |
| 7,265,098 B2 | 9/2007 | Miller et al. | |
| 2003/0108511 A1 * | 6/2003 | Sawhney | 424/78.08 |
| 2004/0018238 A1 | 1/2004 | Shukla | |
| 2005/0048115 A1 | 3/2005 | Mangena et al. | |
| 2007/0248642 A1 * | 10/2007 | Dornish et al. | 424/423 |
| 2007/0280990 A1 | 12/2007 | Stopek | |
| 2007/0299155 A1 | 12/2007 | Carpenter et al. | |
| 2008/0300319 A1 * | 12/2008 | McIntyre | 514/766 |
| 2009/0263468 A1 * | 10/2009 | McAnulty et al. | 424/443 |

FOREIGN PATENT DOCUMENTS

| | | | | |
|---|---|---|---|---|
| EP | 1 666 518 | | 6/2006 | |
| ES | WO2007/023186 | * | 3/2007 | ........... C07D 241/44 |
| WO | WO 01/82937 | | 11/2001 | |
| WO | WO 2004/020473 | | 3/2004 | |
| WO | WO 2007/029913 | | 3/2007 | |

OTHER PUBLICATIONS

Nho, Y. C.; Park, K. R. "Preparation and Properties of PVA/PVP hydrogels containing chitosan by Radiation" J. of Applied Polymer Science, 2002, v. 85, 1787-1794.*

Batchelor "Novel Bioadhesive Formulations in Drug Delivery", The Drug Delivery Co. Report Autumn/Winter 2004, PharmaVentures Ltd. 4 pgs.

Nappi et al., "Prevention of adhesions in gynaecological endoscopy", Human Reproduction Update, vol. 13, No. 4, pp. 379-394 (2007).

Tianyi Ke et al., "Starch, Poly(lactic acid), and Poly(vinyl alcohol) Blends", J. of Polymers and the Environment, vol. 11, No. 1, pp. 7-14 (2003).

Search report for PCT/US2010/046529, mailed May 31, 2011, 13 pgs.

Supplementary European Search Report for EP10815827, mailed Mar. 4, 2013, 8 pgs.

Ravi Kumar et al., "Preparation and characterization of cationic PLGA nanospheres as DNA carriers", Biomat. vol. 25, No. 10 pp. 1771-1777 (2004).

Wischke et al., "Stable cationic microparticles for enhanced model antigen delivery to dendritic cells", J. of Controlled Release, vol. 114, No. 2, pp. 359-368 (2006).

Communication pursuant to Article 94(3) EPC from the European Patent Office for European Patent Application No. 1081582.0 mailed Jun. 25, 2014, 5 pages.

Communication pursuant to Article 94(3) EPC from the European Patent Office for European Patent Application No. 1081582.0 mailed Sep. 28, 2015, 3 pages.

Reply to Official Communication pursuant to Art. 94(3) dated Jun. 25, 2014, for European Patent Application No. 10815827.0, mailed Dec. 24, 2014, 11 pages.

Reply to Official Communication pursuant to Art. 94(3) dated Sep. 28, 2015, for European Patent Application No. 10815827.0, mailed Jan. 27, 2016, 5 pages.

Response to Official Communication pursuant to Article 161(2) and 162 EPC dated Apr. 12, 2012, for European Patent Application No. 10815827.0, mailed Oct. 8, 2012, 10 pages.

Decision for Patent Grant for Japanese Patent Application No. 2012-526927, mailed Jul. 7, 2015, with English Translation, 4 pages.

Notice of Reason for Rejection for Japanese Patent Application No. 2012-526927, mailed Sep. 2, 2014, with English Translation, 5 pages.

Proposed claim set and correspondence between Japanese counsel for Japanese Patent Application No. 2012-526927, mailed Feb. 13, 2015, 12 pages.

Domnina, Yuliya A. et al., "Spray-dried lipid-hyaluronan-polymethacrylate microparticles for drug delivery in the peritoneum", Journal of Biomedical Materials Research Part A, published online Feb. 6, 2008, pp. 825-831.

Ferland, R. et al., "Evaluation of a sprayable polyethylene glycol adhesion barrier in a porcine efficacy model", Human Reproduction, Dec. 2001, vol. 16, No. 12, pp. 2718-2723.

Yeo, Yoon et al., "Polymers in the prevention of peritoneal adhesions", European Journal of Pharmaceutics and Biopharmaceutics, Jan. 2008, vol. 68, pp. 57-66.

Zong, Xinhua et al., "Prevention of Postsurgery-Induced Abdominal Adhesions by Electrospun Bioabsorbable Nanofibrous Poly(lactide-co-glycolide)-Based Membranes", Annals of Surgery, Novmeber 2004, vol. 240, No. 5, pp. 910-915.

* cited by examiner

Step 1
Biodegradable polymer or polymers is
dissolved into an organic or inorganic solvent.

Step 2
Solution is sprayed and dried to produce
particles of the biodegradable polymer.

Step 3
Particles of biodegradable polymer are blended with
particles of water soluble polymer to produce
a biodegradable and water soluble particle mixture.

FIG. 3

Step 1
Prepare two separate polymer solutions:
one solution is a biodegradable polymer dissolved in a first solvent and
other solution is a water soluble polymer dissolved in a second solvent

Step 2
Two solutions are mixed to form an emulsion containing two liquid phases.

Step 3
Spray dry emulsion to form particles

FIG. 4

SPRAYABLE POLYMERS AS ADHESION BARRIERS

CROSS REFERENCE TO RELATED APPLICATION

This application claims benefit of and incorporates by reference U.S. Patent Application No. 61/237,669 which was filed on Aug. 27, 2009.

FIELD OF THE INVENTION

This invention relates generally to adhesion barriers and in particular to sprayable and biodegradable polymer adhesion barriers for prevention of post-operative surgical adhesion formation.

DESCRIPTION OF THE RELATED ART

Post-operative surgical adhesions are a normal part of the surgical healing processes. Many adhesions are desired, and are an integral and important part of the healing of the surgical field. However, adhesions can also result in unwanted scar tissue between vital structures in the body and can result in significant post-operative surgical problems or morbidity. Such adhesions can significantly impact an individual's health, well-being and quality of life. The formation of post-operative surgical adhesions in the abdomen can lead to chronic pain, infertility, and small bowel obstruction (SBO). Adhesions after thoracic and cardiac surgeries can lead to serious consequences during subsequent re-operative cardiothoracic procedures.

The incidence of adhesions forming after surgical procedures is 100%, with less than 5% of adhesions being caused by inflammation. Adhesions form after all types of surgeries (abdominal, pelvic, cardiac, thoracic, spinal, plastic, hand, and knee). In the USA, the cost of abdominal and pelvic adhesions to the healthcare system in 1998 was estimated at $1.6 billion based on 5.6 million surgical procedures deemed "at risk" for developing postoperative related surgical complications.

Post-operative adhesions are a common, expensive problem for patients and the healthcare system. Various approaches have been considered to reduce or eliminate post-surgical adhesions. Such approaches include minimizing trauma to the tissue and tissue exposure to foreign body, and placing physical barriers between injured tissue. It has been suggested that separating the raw to prevent tissue surfaces from coming into contact with each other during the healing process significantly minimizes adhesion formation. As the healing process takes weeks to months, it will be ideal to keep the surfaces apart, at their natural locations, without coming into contact with each other during the period of healing. Physical barriers are helpful in this regard as long as they can be biocompatible and preferably biodegradable. Additionally, any such barrier should be easy to use and fit in with commonly used surgical procedures and protocols.

In the case of physical barriers, one of the more traditional methods involves placing a thin polymer-based film at the surgical site, usually upon the completion of the surgery. Such a method is presently marketed by Genzyme Biosurgery (Seprafilm®) and Cryolife (CardioWrap®). Limitations of such a method, however, are that the film must be cut to correspond to the desired site which adds time to surgery, the membranes are uniform and cumbersome to work with, difficult to configure to the infinite geometric configurations of the human body, and often difficult to place in hard to reach areas within the surgical field.

Several liquid solutions have also been marketed as adhesion prevention systems. Adept®, developed by Baxter, for example and Resolve®, developed by Synthemed, are liquids that can be introduced directly to the intraperitoneal cavity. Specifically, they are used as an instillate after the surgery, and the entire site is washed with the solution. However, since these products are liquid, they do not remain at the surgical site for very long past their introduction into and around the surgical site. As mentioned earlier, it is highly desirable for the material to be present and provide the barrier function for a pre-determined time period, which could be many weeks.

Gel-based adhesion barriers have been developed to overcome the shortcomings discussed above. SprayGel® by Confluent, for example, is a spray composed of two polymers that combine upon spraying to create a film on the surgical site. Confluent Surgical markets a similar product, whereby two liquids are combined prior to application to the surgical site.

An additional short-coming of the products mentioned above is their early absorption within the surgical field. It is desirable to have the adhesion barrier absorb over time, after fibrin and collagen have been formed to prevent adhesion. This generally takes between 30-60 days and could be longer in patients with impaired wound healing. The current gel-based absorbable products are generally absorbed within one week, and thus only prevent adhesions in the early phase of healing. Thus, some adhesion still occurs after the product has been fully absorbed. The adhesion barrier film Cardiowrap is present up to 60 days, but has the shortcomings of the film-based barrier discussed above.

Another shortcoming of the mentioned products is the effectiveness of the particles in forming a cohesive film that can resist or prevent tissue growth or penetration through these barriers. The use of overlapping biodegradable particles that are capable of forming an effective barrier has thus far been ignored.

Ke and Sun describe blends of poly(vinyl alcohol) with poly(L-lactide) which have a higher water absorption than poly(L-lactide) alone. (Starch, Poly(lactic acid) and Poly (vinyl alcohol) Blends, Journal of Polymers and the Environment, Vol. 11, No. 1, (January 2003) They also show that blends of starch/poly(vinyl alcohol)/poly(L-lactide) have improved compatibility and mechanical properties over a starch/poly(L-lactide) blend.

Despite advances in the field, additional improvements are desirable. In particular, it would be advantageous to provide an adhesion barrier that is deliverable as an aerosol or by brushing. This will allow direct and exact application to the desired sites, with minimal or no application to areas where adhesion is desired. Such a product would have the advantages of being easier to store than a liquid or gel, while having greater contact with the desired treatment site than a liquid. It will be manufactured to provide prolonged barrier protection. It may effectively use particles that are capable of overlapping while forming an effective barrier. It may also contain therapeutic agents to allow for delivery over time to a specific area of the surgical field. Such an adhesion barrier would be simultaneously easy to use, efficacious and cost effective. At least some of these objectives will be met by the inventions described hereinafter.

SUMMARY OF THE INVENTION

Various embodiments of the present invention include a formulation for generating an adhesion barrier comprising:

a plurality of particles comprising a polymer combination, wherein the polymer combination comprises at least one biodegradable polymer and at least one water soluble polymer, wherein when the formulation of particles is deposited on a surface of internal body tissue the deposited formulation absorbs moisture from the tissue and forms a film over the surface, and wherein the film is capable of reducing or preventing adhesion of the surface to other body tissue.

Further embodiments of the present invention include a method of generating an adhesion barrier comprising: providing a plurality of particles comprising at least one biodegradable polymer; delivering the plurality of particles to a surface of internal body tissue; and allowing the delivered particles to form an adhesion barrier film on the surface that reduces or preventing adhesion between the surface and other bodily tissue.

Additional embodiments of the present invention include a system for generating an adhesion barrier comprising: a pressurized container comprising an outlet with a valve; and a suspension disposed in the pressured container, wherein the suspension comprises a liquid and a plurality of particles uniformly suspended in the liquid, wherein the particles comprises a polymer combination including a biodegradable polymer and a water soluble polymer, wherein the liquid has a boiling point such that the liquid evaporates immediately upon exposure to ambient or atmospheric conditions, wherein upon opening the valve the suspension is released through the outlet and the liquid immediately evaporates which forms a dispersion of the particles in air.

Other embodiments of the present invention include a method of manufacturing an adhesion barrier comprising: forming a first solution from dissolving at least one biodegradable polymer in a first solvent; forming a second solution from dissolving a water soluble polymer in a second solvent, wherein the first and second solvents are immiscible; blending the first and second solutions to form an emulsion of the first and second solvent; and forming polymer particles from the blend, wherein each of the polymer particles is a blend of the biodegradable polymer and the water soluble polymer.

BRIEF DESCRIPTION OF THE DRAWINGS

The invention has other advantages and features which will be more readily apparent from the following detailed description and the appended claims, when taken in conjunction with the accompanying drawings, in which:

FIG. 1A depicts an exemplary particle structure of a formulation that is a blend of a biodegradable polymer and hygroscopic polymer.

FIG. 1B depicts an exemplary particle structure formulation including a core of a polymer or polymer combination and a shell composed of a different polymer or polymer combination.

FIG. 2 depicts a schematic spray dry system.

FIG. 3 shows an exemplary set of steps for the manufacture of the invention.

FIG. 4 shows an exemplary set of steps for the manufacture of the invention.

FIG. 5A depicts an overhead view of an adhesion barrier film over a selected area of surface region of tissue.

FIG. 5B depicts a cross-sectional view of the film of FIG. 5A.

FIG. 5C depicts an embodiment of an adhesion barrier film with holes or void areas.

FIGS. 6A and 6B depicts schematic delivery configurations.

FIG. 7 depicts an exemplary delivery system for delivery of a formulation of particles from a dry powder.

FIG. 8 depicts an exemplary delivery system for delivering a formulation from a suspension.

FIGS. 9A and 9B depict the swelling of a PLGA/PVA formulation and a PLGA/PEG formulation.

FIG. 10 depicts a photograph of chronic sheep preparation at the time of implant.

FIG. 11 depicts a photograph of a chronic sheep implant at the time of reexploration, 23 days after the initial implant.

FIG. 12 depicts a photograph of a chronic sheep implant at the time of reexploration, 23 days after the initial implant.

FIG. 13 depicts a photograph from the same preparation as in FIG. 12 showing another view of the PLGA film/barrier over the heart (left atrial appendage).

FIG. 14 depicts a photograph of a chronic sheep implant at the time of reexploration, 23 days after the initial implant.

FIG. 15 depicts a photograph from the of chronic sheep implant in FIG. 14.

FIG. 16 depicts a photograph of histologic results of the PLGA membrane (film/barrier) depicted in FIG. 15.

DETAILED DESCRIPTION

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

The various embodiments of the present invention disclose a formulation or composition for generating an adhesion barrier, a method of using said adhesion barrier, and methods of manufacturing said adhesion barrier. Methods of using include, in particular, methods of delivery of the formulation to tissue. Additionally, systems for delivery of the formulations are disclosed. The adhesion barrier that is formed from the formulation is a barrier that prevents the abnormal adhesion or union of tissue surfaces due to formation of new fibrous tissue.

The adhesion barrier is bioabsorbable and can be formulated to lose strength or bio-absorb in specific time frames. Upon delivery, the formulation immediately conforms to tissue and forms a film. The film that is formed sticks to the tissue and does not require suture fixation.

In general, the formulation can be delivered to form a film that provides an adhesion barrier in any part of body on tissue under the skin or within an orifice. Under the skin can include, for example, such as where there is cutting of tissue or where there in an open surgical wound. In exemplary embodiments, the formulation can be delivered to tissue in various types of surgeries. This tissue can be in regions such as pelvic, abdominal, thoracic, orthopedic (e.g., hip and knee), neck, or spine surgeries. The formulation can be delivered under the skin to tissue endoscopically.

The adhesion barrier is a biodegradable film formed from the formulation that includes a polymer or combination of polymers. In preferred embodiments, the formulation includes or is in the form of particles including the polymer or combination of polymers. The particles may be delivered by depositing the particles on living tissue, such as tissue under or beneath the skin. In certain embodiments, the particles prior to delivery are a dry solid or dry powder containing no or substantially no solvent. Substantially no solvent can refer to less than 0.1 wt %, 0.01 wt %, or less than 0.001 wt % of solvent in the particles.

The particles are preferably deposited by directing the particles as a finely dispersed form or as an aerosol onto the tissue. An "aerosol" refers to a system or suspension of particles finely dispersed in a gas or liquid. Finely dispersed refers a system of particles in which agglomeration of the particles in minimized and the particles are dispersed within and are separated by a gaseous medium.

The particles hence form a barrier between the structure to which it is applied and any other structure on the opposing side of the barrier. For example, between the heart and sternum, the heart and lung, the lung and chest wall (perital pleura), the small bowel and abdominal wall (peritoneum), or the liver and colon.

As disclosed in more detail below, the particles can be delivered in various ways such as by application with a brush, or a toothpaste like form. In other embodiments described in more detail below, the formulation can be a gel or liquid that includes the polymer or combination of polymers.

The biodegradable film deposited on the tissue reduces or prevents adhesions from forming between the tissue and other adjacent tissue. The biodegradable film has a lifetime appropriate to a particular treatment application. The film maintains sufficient mechanical strength so that it has mechanical integrity for a period of time. The film then loses mechanical integrity and is eroded or absorbed into the body, disappearing completely from the deposition site over a period of time.

The lifetime of the film can be characterized in terms of the time period that the film maintains sufficient strength to maintain mechanical integrity. Mechanical integrity is the ability of the film to maintain its shape without cracking or maintain a physical barrier that prevents contact of the surface of two organs. The lifetime of the film can also be characterized in terms of the time for the film to be completely eroded or absorbed and removed from the deposition site. The lifetime in terms of strength or to completely absorb can be one to two weeks, two weeks to a month (or 30 days), one to two months (or 60 days), two months to three months (or 90 days), or greater than three months. The film last long enough to allow fibrin and collagen to form to prevent adhesion of tissue.

In some embodiments, a pseudo cellular membrane grows on one or both sides of adhesion barrier film after film formation and becomes a barrier. The body's natural immune response results in the formation of the pseudo membrane over the film and becomes a barrier.

In certain embodiments, the formulation includes a plurality of particles that include or are composed of a polymer or combination of polymers. In some embodiments, the particles include a biodegradable polymer or a combination of at least two biodegradable polymers. The term "polymer" can refer to one type of polymer and can also refer to a combination of polymers. In other embodiments, the particles include a combination of a biodegradable polymer and a water soluble polymer. In these and other embodiments, the biodegradable polymer can be non-water soluble. Preferably, the water soluble polymer is hygroscopic and/or capable of swelling when it absorbs moisture. The combination can include more than one type of biodegradable polymer. The combination can also include more than one type of water soluble polymer. In the case of particles in which individual particles include a biodegradable polymer and a water soluble polymer, the water soluble polymer causes or facilitates swelling of the particle to swell upon contact with tissue.

In general, the water soluble polymer facilitates formation of the film by providing adhesion between particles and adhesion of the film to the tissue or biological substrate. The biodegradable polymer provides structural integrity and strength to the film for a longer period of time that a water soluble polymer in the absence of a biodegradable polymer. The lifetime of the film is determined primarily by the degradation behavior of the biodegradable polymer. Therefore, the biodegradable polymer has a lifetime in terms of mechanical integrity and erosion that is longer than the water soluble polymer. For example, the biodegradable polymer can have lifetimes in water or bodily fluid of at least 30 days, 30 to 60 days, or greater than 60 days.

In other embodiments, the particles can include a biodegradable polymer or combination of biodegradable polymers that are hydrolytically degradable. In some embodiments, the biodegradable polymers are not water soluble. Biodegradable polymers include, for example, aliphatic biodegradable polyesters such as poly(L-lactide-co-glycolide) (PLGA). In additional embodiments, the particles can include a polymer that is both biodegradable and water soluble, such as PVA. In further embodiments, the particles can be made of a polymer that is a block or random copolymer of a biodegradable polymer and a water soluble polymer.

A biodegradable polymer, as used in embodiments of the present invention, refers to a polymer that upon exposure to bodily fluids undergoes chemical degradation that results in chain scission that results in reduction in molecular weight of the polymer. One mechanism of chemical degradation is hydrolytic degradation. Chemical degradation can occur by other means, for example, enzymatic degradation. The degradation of a biodegradable polymer can be characterized by (1) reduction in molecular weight due to chemical degradation; (2) reduction and loss of mechanical properties, in particular strength, due to reduction in molecular weight; (3) loss of mechanical integrity due to deterioration of mechanical properties; and (4) erosion or mass loss from the degraded polymer arising from dissolution of low molecular weight degradation products in the bodily fluid.

A water soluble polymer, as used in embodiments of the present invention, is a polymer that dissolves in water or bodily fluids and is not necessarily subject to chemical degradation upon exposure to moisture or bodily fluids. A water soluble polymer can dissolve in water or bodily fluids, but not be subject to chemical degradation upon exposure to water or bodily fluids, for example, sucrose. A water soluble polymer can dissolve in water or bodily fluids and also be subject to chemical degradation upon exposure to water or bodily fluids, for example, poly(vinyl alcohol) (PVA) A water soluble polymer may be hygroscopic (e.g., polyethylene glycol (PEG)) or may not be hygroscopic (e.g., sucrose). A hygroscopic polymer is a polymer that is capable of absorbing or taking up and retaining moisture from a gas containing moisture, e.g., humid air. A hygroscopic polymer may be capable of swelling or increasing in size upon absorbing moisture. A swellable polymer absorbs moisture and swells or increases in volume due to the absorbed moisture.

After deposition of the particles in moist tissue, the water soluble polymer in the formulation facilitates adhesion or bonding between the deposited particles. This swelling of the particles causes particles to overlap which results in the formation of a film or sections of film that is free of holes or voids which would expose tissue over which the particles are deposited. Additionally, the water soluble polymer facilitates adhesion of the film to the tissue. The water soluble polymers of the formulation also absorbs moisture from the biological tissue upon deposition and facilitates adhesion between particles and between the particles and the biological tissue.

In certain embodiments, the delivery of the formulation of particles includes deposition of small, finely dispersed particles on a selected surface region of tissue. The manner of deposition and fine dispersion of particles allow the deposited particles to develop an intimate, conformal contact with the tissue surface. The formulation exhibits wetting and swelling resulting in spreading of the formulation over the tissue surface and formation of an adhesion film or barrier on the tissue surface that has intimae contact with the tissue surface. The swelled polymer in the film provides strong adhesion or bonding with biological tissues with the help of the surface tension and forces that exist at the site of adsorption or contact.

The present invention includes several embodiments of the combination of the polymers. In some embodiments, a particle of the plurality of particles can include a combination of biodegradable and water soluble polymers. FIGS. 1A-B depict embodiments of polymer combinations in particles. In FIG. 1A, the formulation includes particles such as particle 5 that is a blend or mixture 10 of a biodegradable polymer and a water soluble polymer, where the particle can be made partially or entirely of this blend. In some embodiments, the biodegradable polymer is non-water soluble. In these embodiments, the relative composition (e.g., by weight, volume) of the biodegradable and water soluble polymers in the formulation is determined by the composition of the polymers in the blend. In such embodiments, a particle of the plurality of particles can be a homogeneous blend or mixture of the biodegradable and water soluble polymers. In some embodiments, the biodegradable and water soluble polymer are miscible. Miscible refers to the ability of the polymer combination to mix homogeneously on a molecular level. In other embodiments, the biodegradable and water soluble polymers are immiscible and not capable of forming a molecular homogeneous blend. Immiscible polymer combinations can be mixed or blended, but tend to separate into separate polymer phases, and thus cannot be mixed homogeneously on a molecular level. Therefore, in such embodiments, the combination can be a homogeneous two or more phase dispersion of biodegradable and water soluble polymer phases. The number of phases depends on the number of polymers that cannot be mixed homogeneously on a molecular level.

In additional embodiments, depicted as FIG. 1B, the formulation includes particles such as particle 12 that includes a core 14 composed partially or entirely of a polymer or polymer combination and a shell 16 composed partially or entirely of a different polymer or polymer combination. In one embodiment, the core is composed of a biodegradable polymer(s) and the shell is composed of a water soluble polymer(s). In another embodiment, the core is composed of a water soluble polymer(s) and the shell is composed of biodegradable polymer(s). In these additional embodiments, the relative composition of the biodegradable and water soluble polymer in the formulation is the relative weight or volume of the respective polymers in the core and the shell. In further embodiments, the core can be composed of a blend or mixture of water soluble and biodegradable polymer, as described above, of a biodegradable polymer and a water soluble polymer and the shell is a water soluble or biodegradable polymer.

In further embodiments, the polymer combination in the formulation is a mixture of at least two pluralities of particles, the first and second pluralities being made of different kinds of polymers or polymer combinations. In a particular embodiment, one plurality of particles is composed of a biodegradable polymer and another plurality of particles is composed of water soluble polymer. The relative composition by weight or volume of the biodegradable and water soluble polymers is the relative weight or volume of the two plurality of particles.

In general, it is desirable for the adhesion barrier or film to be relatively thin. In order to develop a relatively thin film and provide intimate contact with the tissue surface, relatively small particle size may be used in the formulation. The mean particle size in the formulation can be 50 nm to 500 microns, or more narrowly, 700 nm to 200 microns.

The types of biodegradable and water soluble polymers, the combination thereof, and the composition thereof influence the quality of the film that is formed, the degree of adhesion of the film, and the lifetime of the film. In some embodiments, the formulation can be 1-99, 10-90, 20-90, 30-90, 40-90, 50-90, 60-90, 70-90, 10-80, 10-70, 10-60, 10-50, 10-40, 10-30, 20-80, 30-70, or 40-60 wt % biodegradable polymer or combinations of such biodegradable polymers. In some embodiments, the composition of the formulation can be 10-90, 20-90, 30-90, 40-90, 50-90, 60-90, 70-90, 10-80, 10-70, 10-60, 10-50, 10-40, 10-30, 20-80, 30-70, or 40-60 wt % water soluble polymer or combination of water soluble polymers.

The biodegradable polymers can include synthetic and naturally occurring hydrolytically degradable polymers. The synthetic hydrolytically biodegradable polymer can include hydrolytically degradable polyesters including poly(L-lactide-co-glycolide) (PLGA). Exemplary naturally occurring biodegradable polymers include chitosan. Exemplary water-soluble polymers include poly(ethylene glycol) (PEG), PEG block polymers, such as di-block or tri-block of PEG/PLGA, PEG/PLA polymer with PEG segment at the end, PEG random or alternating copolymers, such as PEG/PLGA copolymer, sucrose, starch, alginate, polyvinylpyrrolidone (PVP), and poly(vinyl) alcohol (PVA). PVA is an exemplary hygroscopic polymer that is swellable and chemically degradable. With the exception of sucrose, all of the above-mentioned water soluble polymers are hygroscopic.

The degradation behavior of the film, in particular, the time for the strength of the film to degrade resulting in loss of mechanical integrity of the film or for complete erosion of the film can be tuned through variation of the ratio of lactide to glycolide in the PLGA copolymer. As the mole percent of L-lactide (LA) decreases from 100% or increases from 0%, the crystallinity tends to decrease, resulting in a decrease in strength. Additionally, it is known that the in vitro degradation time of PLGA decreases as the mole percent of LA decreases from 100% or increases from 0%. Therefore, the ratio can be changed to provide for different degradation rates and amounts of crystallinity for different treatment periods. In general, the PLGA in a formulation can be between 10% LA/90% GA to 85% LA/15% GA, where the values are expressed in terms of mole percent. Particular PLGA compositions that may be used include 10/90 PLGA, 50/50 PLGA, 70/30 PLGA, 85/15 PLGA, any of these compositions ±3 mole %, and any commercially available compositions identified as having these compositions. A 50/50 PLGA composition may provide a film strength lifetime of between one to two weeks. A 70/30 PLGA composition may provide a film strength lifetime of between 30 and 60 days.

Various combinations of biodegradable polymers with water soluble polymers can be used to obtain desired degradation properties and adhesion. The formulation can include any combination of one or more of the disclosed biodegradable polymers and one or more of the disclosed water soluble polymers. The present invention includes any combination of the disclosed water soluble polymers.

The formulation can include various combinations of types of polymers including:
  biodegradable polymers and water soluble (hygroscopic or non-hygroscopic) non-chemically degradable polymers;
  biodegradable polymers and water soluble chemically degradable polymers;
  biodegradable polymers, hygroscopic water soluble non-chemically degradable polymer, and non-hygroscopic water soluble polymer, and
  biodegradable polymers, (hygroscopic or non-hygroscopic) non-chemically degradable water soluble polymers, and chemically degradable water soluble polymers.

In the above combinations, the water soluble polymers can be hygroscopic or non-hygroscopic.

In some embodiments, the formulation can include any one of the disclosed compositions of PLGA and one or more of the disclosed water soluble polymers. In particular, the formulation can include PLGA and any of the combinations of water soluble polymers described in the above. Exemplary combinations include PLGA with PVA, PEG, starch, alginate, PVP, or any combination thereof. In the formulation, PLGA can vary from 100 wt % to 1 wt % and 99 wt % to 1 wt % of the water soluble polymer or water soluble polymer combination, or more narrowly 10-15 wt %, 15-25 wt %, 25-35 wt %, 35-55 wt %, 55-70 wt %, or 70-90 wt % PLGA. For example, a formulation could include 50 wt % PLGA, 25 wt % PVA and 25 wt % starch.

In additional embodiments, the formulation can include any one of the disclosed compositions of PLGA, another biodegradable polymer, such as Chitosan, and one or more water soluble polymers.

Exemplary polymer combinations for the adhesion barrier formulation include 70/30 PLGA/PVA; Chitosan/PVA; 70/30 PLGA/Chitosan/PVP; Chitosan/PVP; 70/30 PLGA/PEG; 70/30 PLGA/Starch; 70/30 PLGA/PEG copolymer/PEG; 70/30 PLGA/PEG copolymer/PLGA/PVA; 70/30 PLGA/PEG copolymer/PEG/70/30 PLGA; PLGA/Sucrose/PEG; Chitosan/PVA; Chitosan/PVP; PLGA/PVP; and PLGA/Alginate. The weight average molecular weight (Mw) of the PLGA copolymer used in the formulations is 600 to 300,000 Daltons, or more preferably, between 6,000 to 200,000 Daltons. Alternatively, the intrinsic viscosity of the PLGA polymers is between 0.2 and 4.0, or preferably, between 0.8 and 1.2. The Mw of the PEG is between 1000 and 100000 Daltons. The Mw of the Chitosan is between 10000 and 300000 Daltons. The Mw of the PVP is between 6000 and 300000 Daltons.

The water soluble polymer and biodegradable polymer combination provides synergism in the formation of a suitable adhesion barrier film. The water soluble polymer facilitates or provides adhesion between particles and between the formed film and the tissue. Additionally, the water soluble polymer also causes swelling of the particles so that the particles overlap and form a continuous, uniform film free of voids or holes. The biodegradable polymer provides strength and mechanical integrity to the film and increases the life time of the film. A suitable adhesion barrier, i.e., a film that is uniform, free of voids and has sufficient strength and mechanical integrity for a desired time period is provided by a formulation with an appropriate amount each type of polymer. These characteristics or features provided by each of the types of polymer are balanced to provide a suitable film. For example, a film that has insufficient strength or has shorter lifetime than desired can result from too much water soluble polymer and insufficient biodegradable polymer.

A measure of the swelling is given by the water uptake of the particles. The water uptake can be between 1-80%, or more narrowly, 20-30 wt %. Water uptake is defined as the maximum amount of water, expressed in terms of wt % of water in the particle, absorbed by the particle when exposed to a moisture. The inventors have found that the water uptake of particles between 10-30 wt %, in particular, provides for formation of a suitable film.

As indicated above, in additional embodiments, the particles can be made of a block polymer or random copolymer including a biodegradable polymer block and a water soluble polymer block. The physical state of such a block copolymer depends on factors such as the weight ratio of the biodegradable and the water soluble polymers and the molecular weight of the blocks. In some embodiments, the weight ratio and molecular weights of the polymers is selected so that particles made from the block copolymer is a solid (at room or ambient temperature) and not a liquid, gel, paste, or liquid. Room or ambient temperature is typically between 20-30° C. or more narrowly 23-27° C., or at or about 25° C. The block copolymers can be diblock, triblock, star block, or, generally, branched block copolymers.

In exemplary embodiments, the block copolymer can include PLGA blocks and PEG blocks. A solid block copolymer formulation for particles may be a diblock copolymer with a PLGA:PEG weight ratio of 99:1 to 50:50. The molecular weight (weight average) of PLGA may be between 6000 and 500000 Daltons and PEG between 1000 and 10000 Daltons. A solid block copolymer formulation for particles may be a triblock copolymer with PLGA on two ends with a PLGA:PEG weight ratio of 99:1 to 50:50. The molecular weight (weight average) of PLGA may be between 6000 and 500000 Daltons and PEG between 1000 and 10000 Daltons. A solid block copolymer formulation for particles may be a triblock copolymer with PEG on two ends with a PLGA:PEG weight ratio of 99:1 to 50:50. The molecular weight (weight average) of PLGA may be between 6000 and 500000 Daltons and PEG between 1000 and 10000 Daltons.

In some embodiments, the biodegradable polymer can facilitate adhesion of the film to body tissue. For example, Chitosan is known to have relatively strong adhesion to internal biological tissue. In additional embodiments, the water soluble polymer may have a relative weak interaction, and thus, poor adhesion with the biological tissue. For example, alginate has end groups that are expected to have a relatively weak interactions with biological tissue. Thus, a formulation with the combination of Chitosan and alginate may have strong adhesion to biological tissue.

Examples of biodegradable polymers that may be suitable for use with the formulations and methods described here include, but are not limited to, aliginate, cellulose and ester, dextran, elastin, fibrin, hyaluronic acid, polyacetals, polyarylates (L-tyrosine-derived or free acid), poly($\alpha$-hydroxy-esters), poly($\beta$-hydroxy-esters), polyamides, poly(amino acid), polyalkanotes, polyalkylene alkylates, polyalkylene oxylates, polyalkylene succinates, polyanhydrides, polyanhydride esters, polyaspartimic acid, polybutylene diglycolate, poly(caprolactone), poly(caprolactone)/poly(ethylene glycol) copolymers, poly(carbonate), L-tyrosine-derived polycarbonates, polycyanoacrylates, polydihidropyrans, poly(dioxanone), poly-p-dioxanone, poly(epsilon-caprolactone), poly(epsilon-caprolactone-dimethyltrimethylene carbonate), poly(esteramide), poly(esters), aliphatic polyesters, poly(etherester), poly(ethylene glycol)/poly(orthoester) copolymers, poly(glutarunic acid), poly(glycolic acid), poly(glycolide), poly(glycolide)/poly(ethylene glycol) copolymers, poly(glycolide-trimethylene carbonate), poly(hydroxyalkanoates), poly(hydroxybutyrate), poly(hydroxybutyrate-co-valerate), poly(imino carbonates), polyketals, poly(L-lactic acid), poly(L-lactic acid-co-glycolic acid), poly(L-lactic acid-co-glycolic acid)/poly(ethylene glycol) copolymers, poly(L-lactide), poly(L-lactide-co-caprolactone), poly(DL-lactide-co-glycolide), poly(L-lactide-co-glycolide)/poly(ethylene glycol) copolymers, poly(L-lactide)/poly(ethylene glycol) copolymers, poly(L-lactide)/poly(glycolide) copolymers, polyorthoesters, poly(oxyethylene)/poly(oxypropylene) copolymers, polypeptides, poly(DL-lactic acid), poly(DL-lactic acid-co-glycolic acid), poly(DL-lactic acid-co-glycolic acid)/poly(ethylene glycol) copolymers, poly(DL-lactide), poly(DL-lactide-co-caprolactone), poly(DL-lactide-co-glycolide)/poly(ethylene glycol) copolymers, poly(DL-lactide)/poly(ethylene glycol) copolymers, poly(DL-lactide)/poly(glycolide) copolymers, polyphosphazenes, polyphosphoesters, polyphosphoester urethanes, polypropylene fumarate-co-ethylene glycol), poly(trimethylene carbonate), polytyrosine carbonate, polyurethane, PorLastin or silk-ealastin polymers, spider silk, tephaflex, terpolymer (copolymers of glycolide, lactide or dimethyltrimethylene carbonate), and combinations, mixtures or copolymers thereof.

Additional polymers include poly(N-acetylglucosamine) (Chitin), poly(3-hydroxyvalerate), poly(3-hydroxybutyrate), poly(4-hydroxybutyrate), poly(3-hydroxybutyrate-co-3-hydroxyvalerate), poly(L-lactide-co-caprolactone), poly(DL-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, PVA, PVP, starch, biomolecules (such as fibrin, fibrinogen, cellulose, collagen and hyaluronic acid), polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Several embodiments of making particles of the formulation include dissolving a polymer or polymers in a solvent for the polymer to form a polymer solution. In some embodiments, the particles can be formed from the solution using a spray-dry process.

A solvent for a polymer is a liquid that is capable of dissolving the polymer to form a solution containing the polymer mixed with the liquid on a molecular level with at least a 0.1 wt % concentration of polymer. Some common solvents for PLGA include tetrahydrofuran (THF), acetone, and ethyl acetate. Some solvents for 50/50 PLGA include acetone, methylene chloride, ethyl acetate, chloroform, dimethylformamide (DMF), THF, hexafluoroisopropanol (HFIP), etc. Some solvents for 70/30 PLGA include acetone, methylene chloride, ethyl acetate, chloroform, DMF, THF, HFIP, etc. Solvents for Chitosan include acetic acid or water/acid solvent system.

Spray drying is a method of producing a plurality of particles or dry powder with little or no residual liquid or solvent from a liquid (e.g., a solution) or slurry by rapidly drying the liquid or slurry with a hot gas. A relatively consistent or narrow particle size distribution can be obtained with spray drying. Typically heated air is the heated drying media; however, other gases such as nitrogen, oxygen, carbon dioxide, or argon may be used.

A spray dryer apparatus includes an atomizer or spray nozzle to disperse the liquid or slurry into a controlled drop size spray. Exemplary nozzles include rotary nozzles, single-fluid pressure swirl nozzles, or a two-fluid or ultrasonic nozzles. Drop sizes can be in a range from 50 nm to 500 microns, or more narrowly, from 700 nm to 200 microns diameter range.

Figure 2:
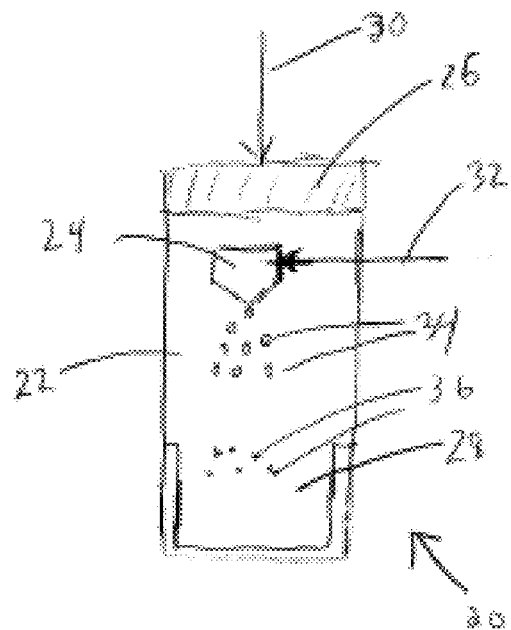

FIG. 2 depicts a schematic spray dry system 20. Spray dry system 20 includes a drying chamber 22, nozzle 24, heater 26, and a particle collector 28. A drying gas enters, as shown by an arrow 30, system 20 via heater 26. A solution containing dissolved polymer is fed into nozzle 24, as shown by an arrow 32, and atomizes the solution and sprays fine droplets 34 with a narrow size distribution into drying chamber 22. The solvent in the droplets evaporates as the droplets fall and become solid particles 36 which are collected in collector 28. The solid particles can be separated using an electrostatic particle collector, filtration, centrifugation, or a combination thereof. The inlet temperature of the heating gas may be controlled by a temperature sensor.

An exemplary spray dryer that may be used to obtain particle sizes in the range 50 nm to 300 microns, for example, for a formulation of the present invention of Chitosan/PVP. Process parameters of the spray dry process include the temperature of the heating gas, droplet size, velocity of droplets, solution concentration, feeding rate, atomizer or atomization pressure, inlet temperature, outlet temperature, etc. The atomization pressure can be 0.01 to 1 MPa, or more narrowly 0.1 and 0.5 MPa. The inlet temperature can be 50 to 300° C., or more narrowly 100 and 200° C. The outlet temperature can be −20 to 80° C., or more narrowly between 0 and 50° C. The spray rate can be 0.1 to 5000 ml/min. The conditions will depend on the size of spray dryer, operation temperature and particles size requirement, etc.

A formulation containing a mixture of biodegradable polymer particles and water soluble polymer particles can be made by forming the different types of particles in separate processing steps and physically blending the particles together. An exemplary process for manufacturing the particles for such a formulation is shown in FIG. 3. In Step 1, a biodegradable polymer or polymers is dissolved into an organic or inorganic solvent. A biodegradable polymer or combination of biodegradable polymers may be that provides the film forming properties and desired treatment period of the end product. The resulting solution of biodegradable polymer and solvent can vary in concentration between 0.01 to 25 wt %, or more narrowly, between 0.2 to 10 wt % of biodegradable polymer. In particular, a solution of 70/30 PLGA in acetone or other solvents may be between 0.2 and 10 wt % 70/30 PLGA. In Step 2, the resulting solution is then sprayed and dried to produce particles of the biodegradable polymer.

Particles of water soluble polymer are made in a similar manner. A water soluble polymer is dissolved in water with a concentration of between 0.01 and 25 wt % polymer, or more narrowly, between 0.1 and 10%. Exemplary concentrations of PEG, sucrose, starch can be 1-3 wt %, for example, 2%. A concentration of PVA in a solution is between 0.1 and 10 wt %. A suitable solvent for PVP includes water and a concentration of PVP in a solution is between 0.1 and 10 wt %.

In Step 3, the particles of biodegradable polymer are blended with particles of water soluble polymer to produce a biodegradable and water soluble particle mixture.

A formulation of particles that are a blend or mixture of biodegradable polymer and water soluble polymer can be formed by spray drying an emulsion containing the two types of polymers. An exemplary process for manufacturing such particles of such formulations is shown in FIG. 4. As shown in Step 1, two separate polymer solutions are prepared, one solution being a biodegradable polymer dissolved in a first solvent and the other solution being a water soluble polymer dissolved in a second solvent. The first solvent is typically an organic solvent and the second solvent is typically water or an aqueous solution. The properties of the first and second solvent are such that a two phase liquid mixture is formed. Immiscibility of the first solvent and the second solvent allow the formation of a two phase liquid mixture. The ratio of the amount of biodegradable polymer dissolved in the first solvent and the amount of water soluble polymer dissolved in the second solvent corresponds to the desired ratio of the two polymers in the particles.

For example, PLGA can be dissolved in acetone or chloroform and PEG or PVP can be dissolved in water. Chitosan can be dissolved in an aqueous solution that is acidic, since its solubility is increased in an acidic environment. For instance, an aqueous solution can have between 0.05 and 5 wt % acetic acid.

As shown in Step 2, the two solutions are mixed to form an emulsion containing two liquid phases. The solution having the smaller volume will be dispersed within the solution with the larger volume. The relative volume of the two solutions depends on the concentrations of polymer in each and the desired relative composition of polymers in the particles. For given solution concentrations, the relative volume is adjusted so that the relative amount of the polymer in each solution is the desired relative amount in particles made from the solutions. Specifically, the ratio the volume of solution 1 (V1) to the volume of solution 2 (V2) is:

$$V1/V2 = (p1/p2) \times (C2/C1)$$

wherein p1 and p2 are the weight percent of polymer 1 and polymer 2, respectively, of the polymer blend of resulting particles and C2 and C1 are the concentrations of the solution of polymer 1 and polymer 2, respectively.

For example, 70/30 PLGA and PVA particles (70 wt % PLGA and 30 wt % PVA) can be formed from a 1 wt % PVA solution and a 1-5 wt % solution of PLGA. To obtain 70/30 particles using the 1 wt % PLGA solution, the ratio of the volume of the PLGA solution to the volume of the PVA solution is (70/30)×(1/1) or about 2.33. In this case, the PVA solution will be dispersed in the PLGA solution. Similarly, to obtain 70/30 particles using 5 wt % PLGA solution, the ratio of the volume of the PLGA solution to the volume of the PVA solution is (70/30)×(1/5) which is about 0.47. In this case, the PLGA solution will be dispersed in the PVA solution.

In some embodiments, the aqueous phase is dispersed in the organic phase or alternatively, the organic phase is dispersed in the aqueous phase. In some embodiments, the two solutions are combined slowly and the solutions may be stirred on sonicated with a sonic mixer to facilitate formation of a stable emulsion.

In step 3, a spray dryer is used to form particles from the emulsion. The particles formed will be a blend of the biodegradable polymer and the water soluble polymer, e.g., a blend of PLGA and PVA. The spray drying process is described in detail below.

In some embodiments, a biodegradable polymer and a water soluble polymer can be dissolved in the same solvent. In an exemplary embodiment, Chitosan and a water soluble polymer can be dissolved in an aqueous acidic solution of acetic acid. Particles of Chitosan and the water soluble polymer can be formed from the solution by spray drying.

In additional embodiments, the solution or emulsion containing the biodegradable and water soluble polymer can be concentrated prior to spray drying. In such embodiments, at least some of the organic solvent can be removed, for example, through evaporation. This can be advantageous because this reduces the time required by the spray drying process to form the particles. In spray drying, the time to form particles from a volume of solution or emulsion increases with the volume of solution. In these embodiments, a portion of the organic solvent is evaporated from the emulsion or solution. In some embodiments, a portion of the organic solvent may be removed or all of the organic solvent may be removed. In exemplary embodiments, less than 10 vol %, 10-20 vol %, 20-30 vol %, 30-60 vol %, 60-80 vol %, or 80-100 vol % of the organic solvent can be removed. The evaporation can time can be, for example, performed over a period of 1-8 hours. The evaporation can be performed at room temperature or, alternatively, the emulsion can be heated to a temperature below the boiling point of the organic solvent.

In these embodiment, removal of the organic solvent can result in the formation of a solution, elution, or system having a uniform milky appearance. The milky appearance is due to the presence of fine particles that are a blend of the polymers in the emulsion that are likely in the range of 300 nm to 20 microns. Although particles have formed from previously dissolved polymers, some of the polymers may also remain dissolved in the respective solvents in the emulsion. The milky solution may then be spray dried to form the blended particles from polymer that remains dissolved after mixing the organic and aqueous solutions.

The milky system may be characterized as a colloid or colloidal system or a suspension. A colloid is a type of chemical mixture where one substance is dispersed evenly throughout another. The particles of the dispersed substance are only suspended in the mixture, unlike a solution, where they are completely dissolved within. This occurs because the particles in a colloid are larger than in a solution—small enough to be dispersed evenly and maintain a homogenous appearance, but large enough to scatter light and not dissolve. Because of this dispersal, some colloids have the appearance of solutions. A colloidal system includes at least two separate phases: a dispersed phase (or internal phase) and a continuous phase (or dispersion medium). A colloidal system may be solid, liquid, or gaseous. The particles of a colloidal system have dimensions between 2 to 1000 nm. In the case of a the milky suspension, the polymer particles are the dispersed phase and the solvent(s) are the dispersion medium.

Suspensions are homogeneous mixtures with particles in a continuous phase that have diameters greater than 1000 nm. The size of the particles is great enough so they are visible to the naked eye. Blood and aerosol sprays are examples of suspensions. Suspensions are "murky" or "opaque". They do not transmit light. Suspensions separate on standing.

In other embodiments, removal of the organic solvent can result in the formation of a nonuniform suspension of particles in the solution. The particles of the nonuniform suspension are larger and the particle size is likely in the range of 1 to 150 microns. Dissolved polymer is also still present in the solution. The suspension may then be spray dried to form the blended particles from polymer that remains dissolved.

Whether or not a milky system is formed depends on several factors including the miscibility of polymers, ratio of polymer matrix, solution concentration, mixing speed and vaporization control of solvent, etc.

The particles formed by spray drying the emulsion with the milky appearance result in a formulation with smaller particles than spray drying the suspension. The formulation formed from the former has particles in the range 0.3 to 20 microns and the latter in the range 1 to 150 microns.

Additionally, a particle blend can have more than one biodegradable polymer, more than one water soluble polymer, or a combination thereof. The procedure described above can be generalized to such blends. In an exemplary embodiment, a blend including two water soluble polymers can be obtained by forming a solution containing the two polymers which is mixed with a solution of biodegradable polymer. For example, the particle can contain PVA and PVP or PEG and sucrose. Alternatively, separate solutions of the water soluble polymer can be mixed with the biodegradable polymer solutions. As indicated above, particles can be a blend of more than one biodegradable polymer with a water soluble polymer, for example, PLGA, Chitosan, and a water soluble polymer.

Additionally, a blend including two biodegradable polymers can be obtained by forming a solution containing the two polymers which is mixed with a solution of water soluble polymers. Particles containing a blend of PLGA, Chitosan, and a water soluble polymer can be obtained by mixing a solution of Chitosan with separate solutions of PLGA and the water soluble polymer. Alternatively, an aqueous acidic solution of Chitosan and a water soluble polymer can be mixed with a PLGA solution.

In other embodiments, a solution of two or more biodegradable polymers can be formed by dissolving the polymers in the same solvent. An example is PLGA and PLGA-PEG block polymer which can dissolve in acetone to produce swellable polymer particles. Another example is PLGA polymer which can dissolve into liquid PEG (low molecular weight PEG), for example, PEG with a molecular weight of 400 g/mole (weight or number average).

As discussed above, particles can include or be composed entirely of a block copolymer of a biodegradable polymer and a water soluble polymer. The block copolymer particles can be made from a solution formed by dissolving the block copolymer in a solvent. In one embodiments, the solution can be spray dried to form the particles. In another embodiment, the solvent may be evaporated to allow formation of a suspension of particles in the solution or colloid or an elution. The resulting suspension or colloid or elution can then be spray dried to form the particles. The solvent can be an organic solvent, such as acetone or chloroform. Alternatively, the solvent can be water.

The solvent selection can be based on the solubility of the block copolymer. In one embodiment, a solvent is selected to allow formation of at least a 0.1 wt % of block copolymer solution, between 0.1-1 wt %, or at least 1 wt % block copolymer solution. The solubility of the block copolymer in an organic solvent or water depends on the relative composition of the biodegradable polymer, such as PLGA, and the water soluble polymer, such as PEG. The larger the mole percent of PLGA, the more likely the block copolymer will be soluble or more soluble in an organic solvent. Alternatively, the larger the mole percent of the water soluble polymer, the more likely the block copolymer will be soluble or more soluble in water.

The particle size from spray drying can be influenced or controlled in several ways. The particle size depends process parameters, such as atomization pressure. As shown below in Example 6A, an increase in atomization pressure can increase the particle size. The concentration of the polymer and the relative concentration of the component polymers in the formulation solution can also influence the particle size. Additionally, a surfactant in the formulation solution can influence particle size. The surfactant can be added to the formulation solution prior to spray drying. As indicated in Example 6C, addition of mannitol to PLGA/Chitosan/PVP formulation solution increases the particle size.

In some embodiments, the resulting biodegradable and water soluble particles formed from the methods described herein may be larger than desired for formation of a suitable adhesion barrier film. The particles may be reduced in size through one method, or any combination of methods. For example, the particles are reduced mechanically by grinding in a fine grinding mill. Additionally or alternatively, the particles are reduced chemically by exposure to a solvent that dissolves at least a portion of a polymer in the particles. The exposed particles may then be dried, filtered, or a combination thereof. Alternatively, if a larger particle size is desired, the particles may be compounded to a larger size using methods that include, but are not limited to, compacting, coating, and pelleting.

Further embodiments of the present invention include delivery of the formulation of particles to internal body tissue. The embodiments include depositing the particles on the internal body tissue to allow formation of a thin film over a selected area of the tissue. Upon deposition on the tissue, the particles absorb moisture from the tissue, swell and overlap which result in the formation of a film over the selected area. A sufficient amount of formulation is deposited to form a continuous film over the selected tissue area The film is preferably delivered so that it is relatively uniform in thickness and surface texture over the selected area of tissue. Additionally, the film is preferably free or substantially free of holes or void areas that expose tissue in the selected region. Such exposed areas may be susceptible to the formation of adhesions since they allow tissue to tissue contact. Furthermore, the film is preferably thick enough so that the film maintains mechanical integrity and coverage of the selected area for a desired time frame. A relative uniformity in thickness reduces or prevents the premature exposure of portions of tissue prior to a desired time frame. The thickness of the film is preferably between 300 nm and 800 um, or more narrowly, between 1 um and 200 um. The film should not be so thick that it causes adverse effects such as clumping, and an extreme foreign body reaction, which may in turn result in the development of a thick pseudo-membrane, and hence, be counter-productive to the desired end result. Extreme thickness may also alter the absorption time.

Figure 5A:
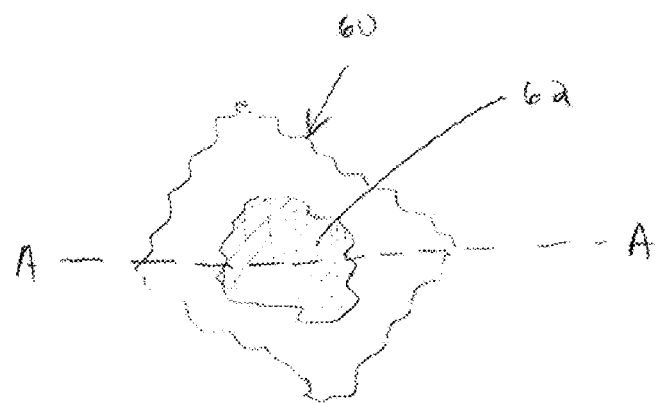
Figure 5B:
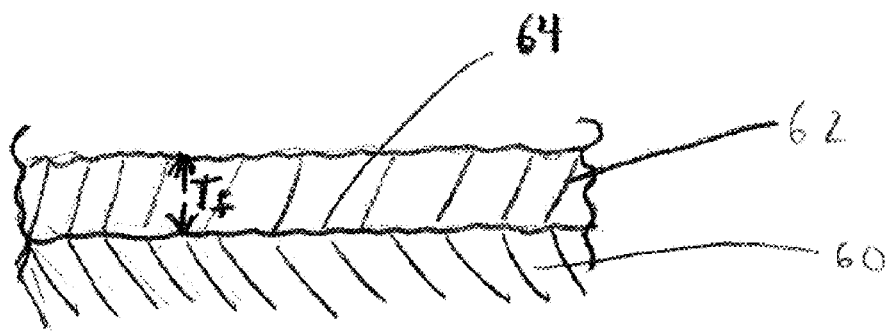
Figure 5C:
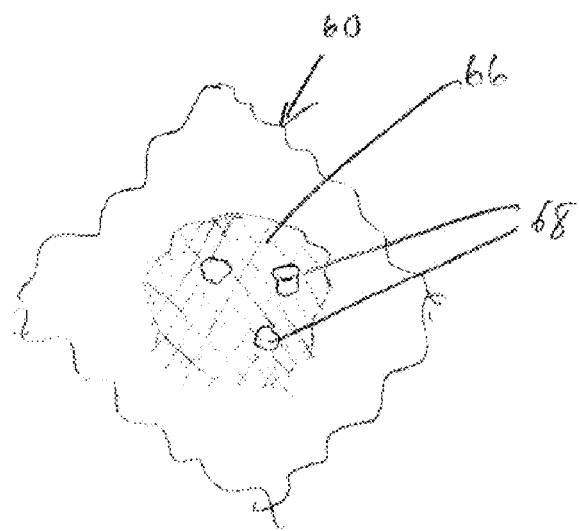

FIG. 5A depicts an overhead view of a surface region 60 of the surface of tissue that includes an adhesion barrier film 62, as described herein, over a selected area of surface region 60. Film 62 is free of any holes or voids and has a relatively uniform thickness. FIG. 5B depicts a cross-sectional view of film 62 showing the thickness, Tf, of film 62 and an interface 64 between film 62 and tissue 60. FIG. 5C depicts another embodiment of a film 66 over tissue region 60 that has holes or void areas 68 that could be due to unsatisfactory delivery of the formulation.

In certain embodiments, the particles are deposited or directed onto the surface of tissue as a finely dispersed suspension or as an aerosol to provide the desirable characteristics described above. The particles may be deposited in a dry form suspended in a gas. Delivery in a manner that reduces or minimizes agglomeration of the particles facilitates formation of a thin film with relative uniform thickness. Additionally, the delivery should be performed in a manner that allows a close intimate contact of particles with the tissue so that a film forms with conformal coverage that has close, intimate contact with the surface. The intimate, conformal contact facilitates strong adhesion of the film to the tissue since it is believed that the particles swell into tissue which allows intermingling of particle molecules and tissue molecules that enhances adhesion. Delivery in the form of particles, followed by swelling and film formation is expected to provide a more intimate, conformal contact with tissue than, for example, a preformed film or sheet applied to the tissue surface.

The synergistic effect of the formulation characteristics and the manner of delivery provide for a film with the desired characteristics. Formulation characteristics include a polymer combination that provides for adhesion of particles to each other and adhesion to tissue, swelling of particles to form a film, and degradation behavior of film that remains for desired time frame.

Figure 6A:
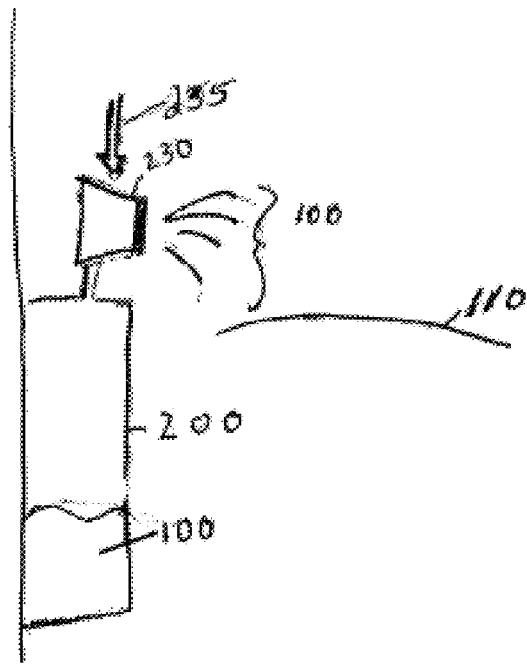
Figure 6B:
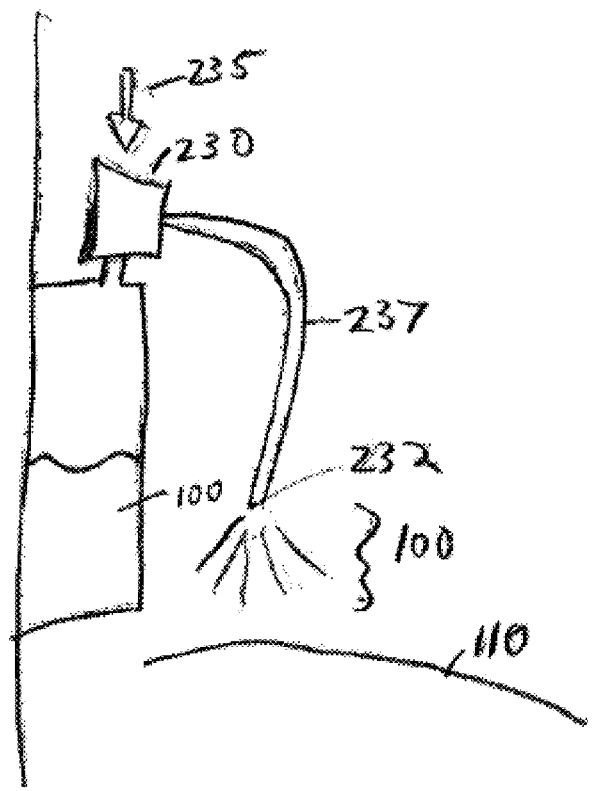

FIGS. 6A and 6B depict schematic delivery configurations. The particles 100 are stored in an aerosol delivery device 200. Aerosol delivery device 200 is any pressurized or unpressurized compartment including a mechanism of propelling the particles from within the delivery device 200 to a selected area of tissue. The delivery device 200 may contain an actuator 230, which, when depressed, as shown by an arrow 235, releases pressure from within the delivery device 200 to propel the particles from within the delivery device to the desired site. Once the particles contact the internal tissue at a surgical site, they will swell to form an adhesion barrier film 110. Optionally, as shown in FIG. 6B, a tube 237 may be connected to actuator 230, to allow greater control and accuracy in the delivery of the particles to the desired site. The distal end 232 can be manipulated to direct particles are specific areas of the tissue.

In some embodiments, the formulation of particles may be delivered from a container in which the particles are stored as a dry powder. The particles may be drawn out of an outlet of the container by a pressure differential between the interior of the container and the outlet, the pressure differential being a lower pressure at the outlet than the interior of the container. The drawn out particles may be directed in the form of a fine dispersion in a gas onto a region of tissue.

In one embodiment, the pressure differential can be created by pressurizing the interior of the container above atmospheric pressure. A valve at the outlet can allow for a controlled release of particles. The particles that are drawn out through the valve can be dispersed through a hose, nozzle, atomizer, or some other means for deposition on the tissue.

In another embodiment, the pressure differential can be created by a stream of gas flowing past the outlet of the container. The particles may be drawn out of the outlet and in the stream of gas in a dispersed form. The dispersed stream of particles may be directed at a selected region of tissue and deposited thereon. In a further embodiment, in addition to the stream of gas, the container may be pressurized above atmospheric pressure to increase the velocity of the stream of gas, which facilitates intimate contact of the particles with tissue when deposited.

Figure 7:
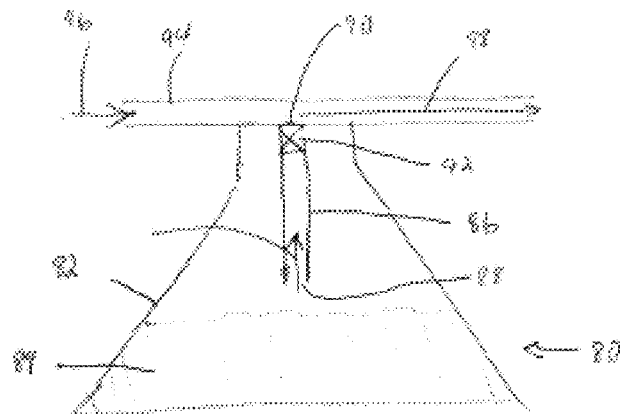

FIG. 7 depicts an exemplary delivery system 80 for a formulation of particles. System 80 includes a container 82 which includes particles 84 in a dry power form. A tube 86 is disposed within container 82 with an inlet 88 and an outlet 90. Container 82 and tube 86 are sealed when not delivering particles. Tube 86 has a valve 92 that allows fluid communication between the interior and exterior of container 82. A tube 94 is positioned to be in fluid communication with tube 86 when valve 92 is open. A stream of gas, as shown by arrow 96, is passed through tube 94. The stream of gas, for example, may come from an oxygen or air supply in an operating room. When valve 92 is opened, particles are drawn out of container 82, as shown by an arrow 88, through tube 86 and into tube 94 by a pressure differential between tube 86 and 94 created by the flow of the stream of gas in tube 94. The particles that are drawn out are dispersed in the stream of gas 96. The dispersed particles, as shown by an arrow 98, pass through tube 94 and then are deposited onto a tissue surface.

In other embodiments, the formulation of particles may be delivered from a pressurized container that includes a suspension of the particles in a liquid propellant. In such embodiments, the particles may be uniformly dispersed within the suspension. The liquid may be selected so that the particles are uniformly dispersed and agglomeration of particles is reduced or minimized. The container may have a valve that allows fluid communication between the interior and exterior of the container so that when the valve is released the suspension is released from the container.

In some embodiments, the propellant is selected so that it is a liquid at room or ambient temperature and the pressure in the container and which immediately evaporates or flashes when it exits the container at atmospheric pressure and room temperature. Therefore, the particles are delivered as a dispersed spray or stream onto the tissue without the liquid propellant. Exemplary liquid propellants include hydrofluoroalkanes (HFA) such as HFA 134 and HFA 227ea.

Figure 8:
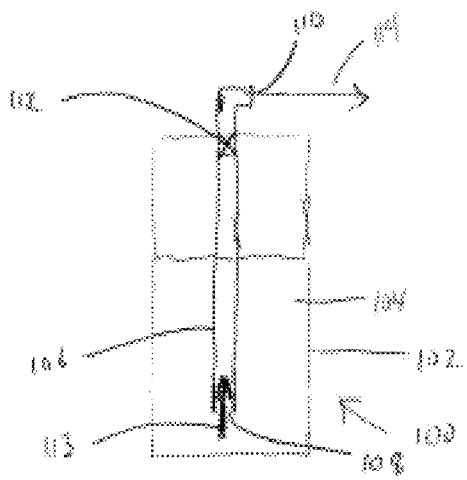

FIG. 8 depicts an exemplary delivery system 100 for delivering a formulation of particles from a suspension. System 100 includes a container 102 which includes a suspension 104 of particles in a liquid propellant. The container is pressurized to a pressure above atmospheric pressure. A tube 106 is disposed within container 102 with an inlet 108 and an outlet 110. Container 102 and tube 106 are sealed when not delivering particles. Tube 106 has a valve 112 which allows fluid communication between the interior and exterior of container 102. When valve 112 is opened, suspension 104 is drawn out of container 102, as shown by an arrow 113, through tube 106. The liquid in the suspension evaporates immediately or flashes and a dispersed stream or spray of particles, as shown by arrow 114, that can be deposited onto a tissue surface.

The present invention includes additional formulations of a combination of biodegradable and water soluble polymers. In one embodiment, the particles can be mixed with a liquid to form a slurry. Exemplary liquids include water, acetone, and alcohol.

In alternative embodiments, the formulation used for forming the adhesion barrier can be a liquid, gel, or paste that includes a biodegradable polymer and a water soluble polymer. In some embodiments, the formulation can be a liquid at a lower temperature and forms a higher viscosity liquid, gel, or paste at higher temperatures. In particular, the formulation can be liquid at room or storage temperature and be a higher viscosity liquid, gel, or a paste at body temperature A liquid formulation can be delivered to tissue by, for example, brushing or spraying the formulation on to the surface of the tissue. A formulation having a transition to a more viscous liquid, gel, or paste at a temperature between room and body temperature will then exhibit such a transition after being applied to the tissue.

A liquid, gel, or paste formulation can be made by dissolving a biodegradable, polymer within a water soluble polymer. The water soluble polymer can be a liquid, gel, or paste. The physical state of the water soluble polymer (liquid, gel, or paste) depends on the molecular weight of the water soluble polymer. A liquid has a lower molecular weight than a gel or paste. An exemplary formulation is PLGA and PEG. A liquid formulation at room temperature can be formed using PEG with a Mw between 300-400 g/mole. PLGA can be mixed or dissolved in the PEG to form a liquid. The liquid formulation can be 1-50 wt % PLGA and 99-50 wt % of PEG. Such a liquid exhibits a transition from a liquid to a gel or paste between room and body temperature and is a gel or paste at body temperature. A gel at room temperature can be formed by mixing PLGA with PEG gel. The Mw of the PEG is between 100 and 1000.

Additional methods may be applied to deliver a formulation to body tissue. In one embodiment, a formulation can be disposed in a squeezable container such as a tube. The formulation can be delivered by squeezing the tube in a manner similar to an ointment. In such embodiments, the formulation may be dry particles, a gel or paste system, or a highly viscous slurry. In other embodiments, a formulation of dry particles, gel or paste, or slurry can be sprayed or brushed onto tissue.

In additionally embodiments, a formulation of particles can be disposed in a container having a delivery end that has a plurality of small holes. The particles are delivered by shaking the container over a selected region of tissue.

Additionally, during any part of the process of making the formulation, other compounds may be added to ameliorate the usability or to provide therapeutic value of the adhesion barrier. For example, a biocompatible dye is added to promote visibility of the adhesion barrier.

Additionally or alternatively, therapeutic agents such as drugs are added, for example by mixing or introducing said drug into the polymer matrix during any of the steps of manufacture.

Exemplary therapeutic agents include hemostatic or anti-hemorrhagic agents to reduce or inhibit bleeding in a selected region of tissue. Hemostatic agents can include those classified as systemic, local, organic, and chemical. Systemic drugs work by inhibiting fibrinolysis or promoting coagulation and include antifibrinolytics, vitamin K, fibrinogen, and blood coagulation factors. Locally-acting hemostatic agents work by causing vasoconstriction or promoting platelet aggregation. Organic agents include thrombin coagulation factor, microfibrillar collagen, and polysaccharides, such as starch. Chemical hemostatic agents include Chitosan, hemCon, zeolites, and styptics. Styptics work by contracting tissue to seal injured blood vessels.

Another type of drug can include chemotherapeutic agents which includes, but are not limited to, paclitaxel, protin-bound paclitaxel, alkylating agents, antimetabolites, anthracyclines, plant alkaloids, topoisomerase inhibitors, and other antitumour agents, plant alkaloids and terpenoids, vinca alkaloids, podophyllotoxin, topoisomerase inhibitors, antitumour antibiotics etc.

An exemplary drug to be introduced in the formulation includes an anti-adhesion agent or an anti-fibrin growth agent. As another example, an anti-inflammatory drug can be added. The anti-inflammatory drug can be a steroidal anti-inflammatory agent, a nonsteroidal anti inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, Clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Additionally, the resulting adhesion barrier composition may be used in conjunction with other types of adhesion barriers such as film adhesion barriers. In this situation, the particles and the film may have varying degrees of biodegradability, or may contain various drugs or drug quantities.

EXAMPLES

Example 1

Particle Size Analysis

The particle sizes of two formulations of particles were measured. The particles were formed by spray drying. Each of the formulations are particles that are a blend of 70/30 PLGA and a water soluble polymer. A pinch of a powder formulation was added to about 3 mL of water in a test tube and mixed well to form uniform dispersion to measure particle size distribution. The dispersed liquid was transferred to a curette and the particles size was determined using Malverns Zeta Sizer obtained Malvern Instruments Ltd, Worcestershire, UK.

TABLE 1

Particle size of formulations.

| Formulation | Mean particle diameter (nm) |
| --- | --- |
| PLGA/PEG (80:20 mole %) | 723.9 |
| PLGA/PVA (80:20 mole %) | 1404.2 |

Example 2

Water Absorption

The water absorption was measured for four formulations of particles that are blends of 70/30 PLGA and a water soluble polymer. A solution of biodegradable and water soluble polymer combination was spread over a surface and allowed to air dry to form a film. The polymer films were carefully removed and allowed dry in an oven at 60° C. for about 12 hours.

The initial weight of the dried films were recorded and immersed into water. The films were removed, blotted with tissue paper to remove any excess water from film, and weighed. The weight gain of the films was calculated and is shown in Table 2.

TABLE 2

Water absorption of formulations.

| Formulation | % wt gain |
| --- | --- |
| PLGA PEG (70:30) | 88.78 |
| PLGA/PVA (70:30) | 67.44 |
| PLGA/PEG (80:20) | 16.00 |
| PLGA/PVA (80:20) | 24.36 |

Example 3

Swelling Properties

Figure 9A:
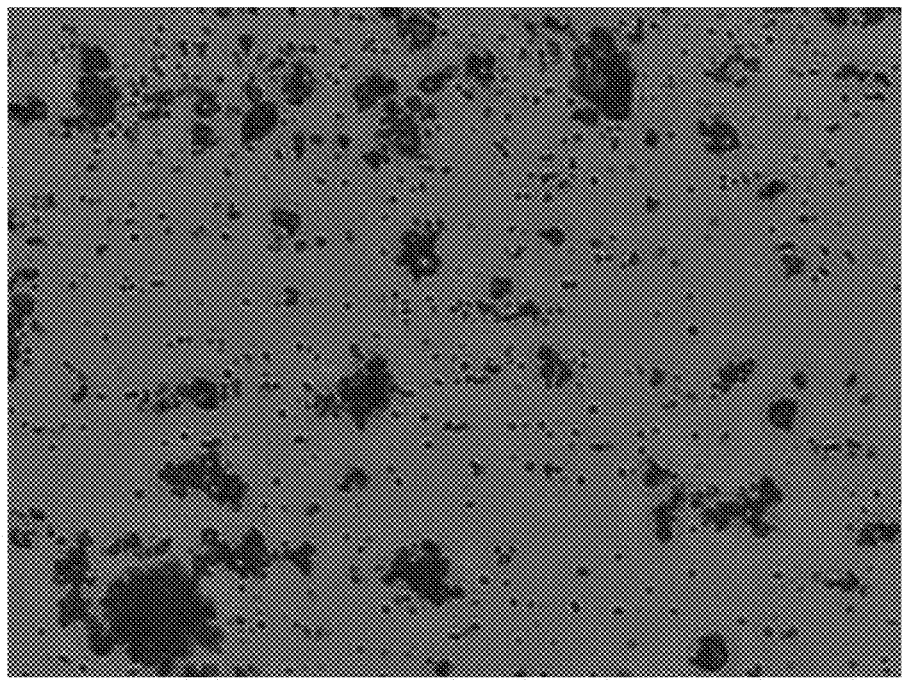
Figure 9B:
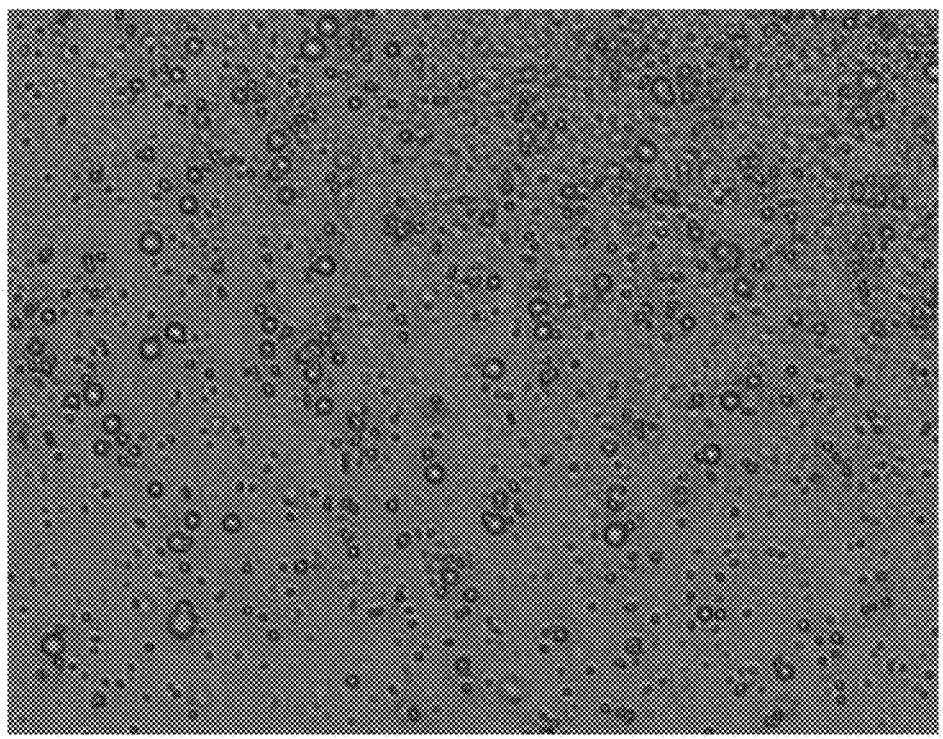
Figure 10:
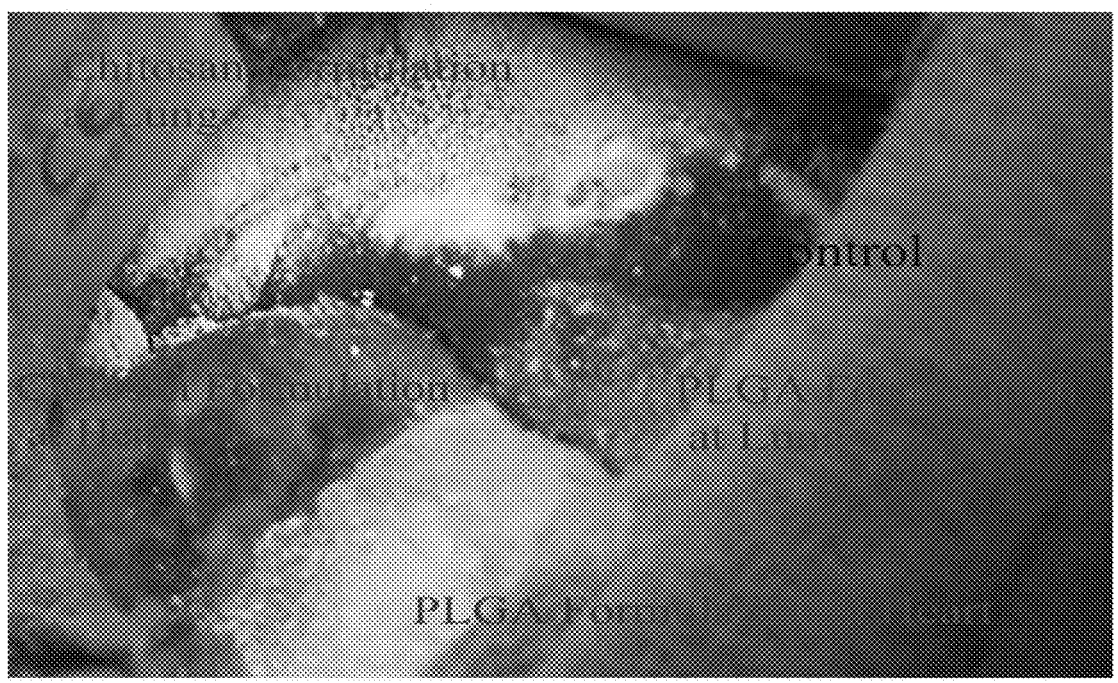
Figure 11:
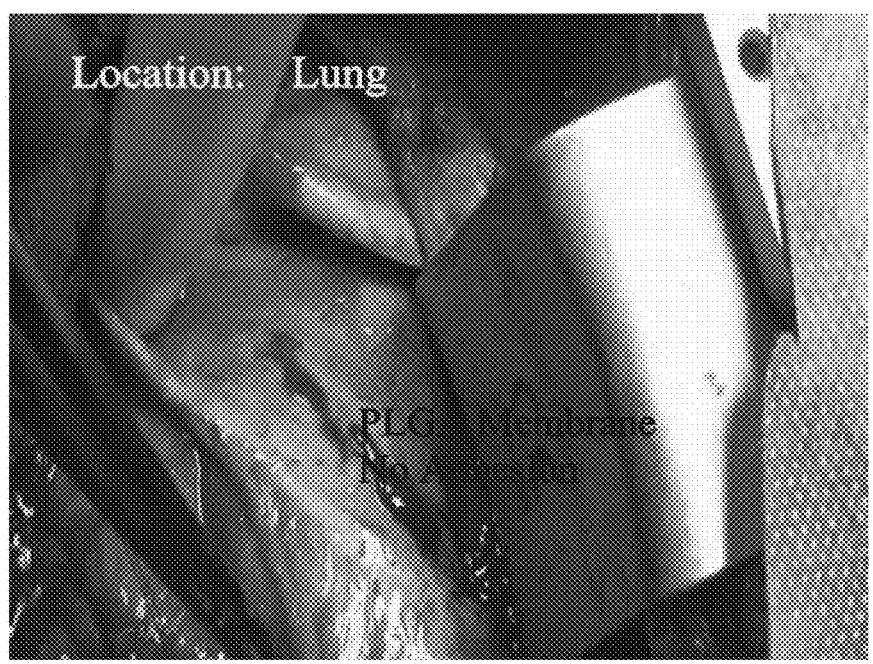
Figure 12:
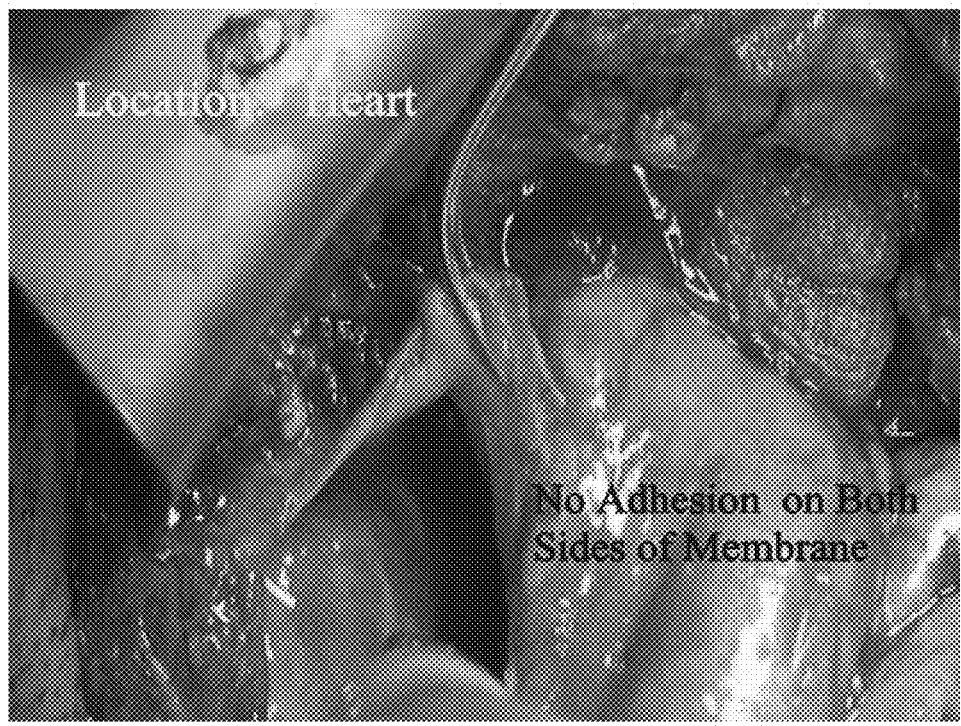
Figure 13:
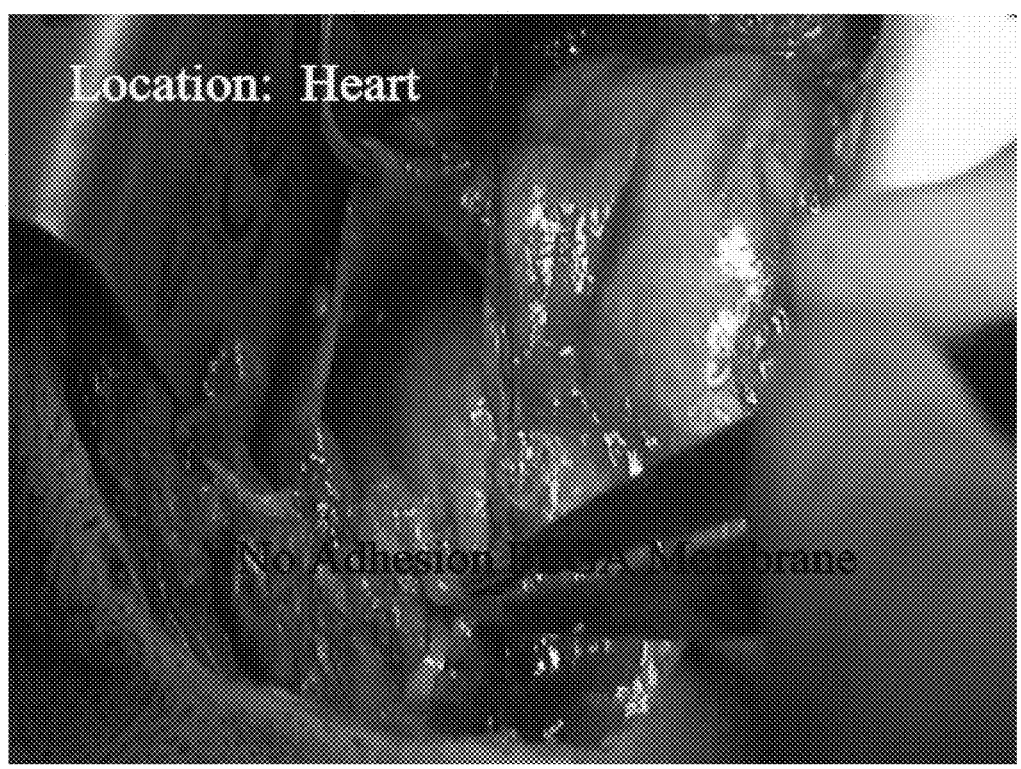
Figure 14:
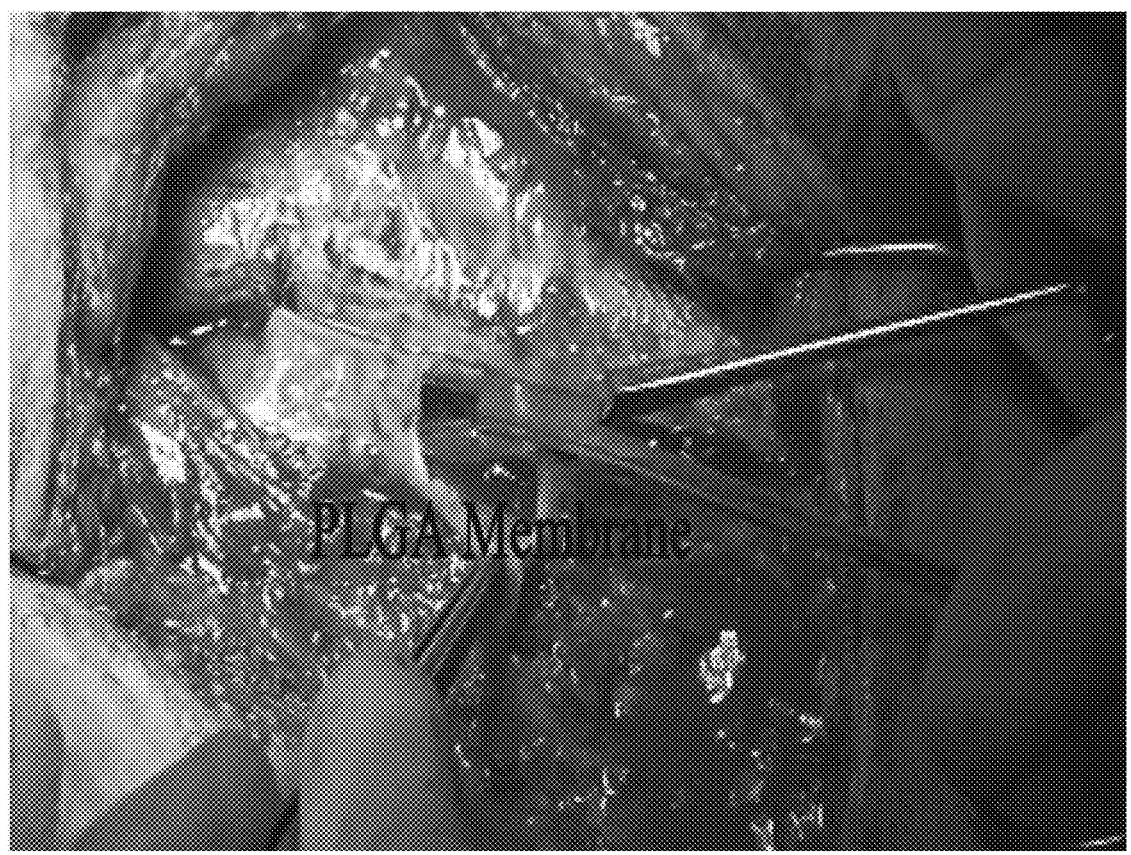
Figure 15:
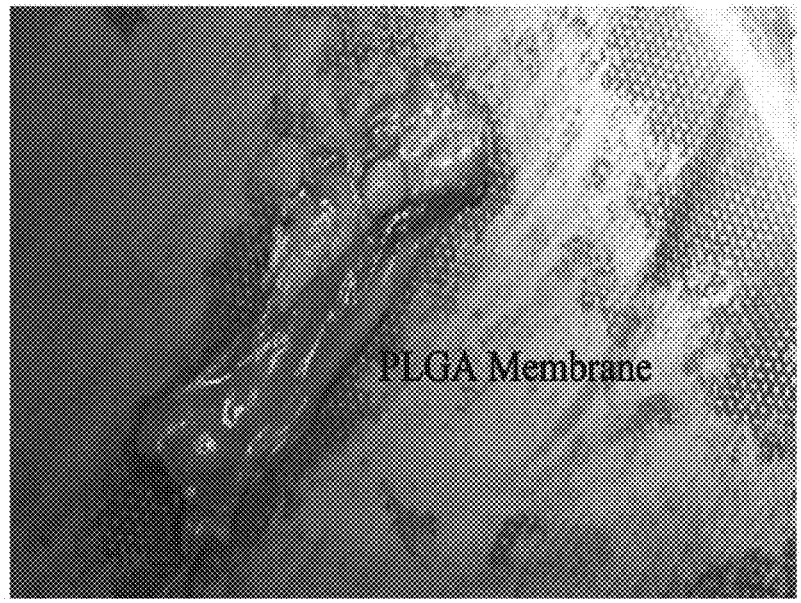
Figure 16:
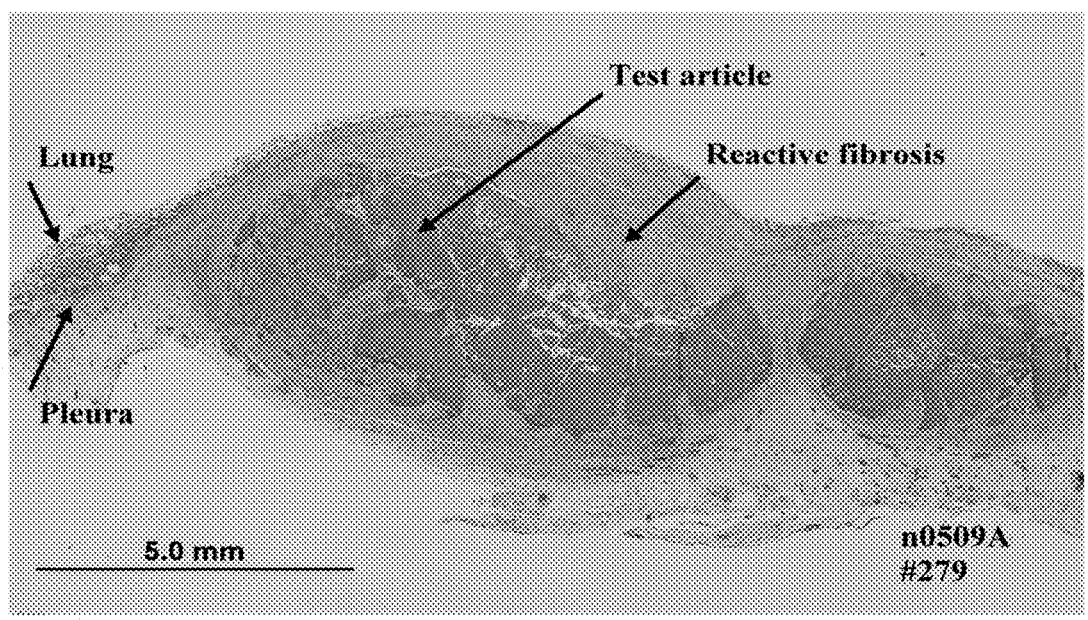

The formulation powders were spread over a microscopic slide and an initial photomicrograph was taken. A few drops of water were slowly added at the edge of the cover slip using a micropipette. Photomicrographs at different intervals were taken to observe any swelling of the particles upon exposure to water. FIGS. 9A and 9B depict the swelling of a PLGA/PVA formulation and a PLGA/PEG formulation, respectively. Both pictures show that water diffused into the particles and particle diameter increased due to swelling.

Example 4

Adhesion Test

Adhesion Test 1:
The formulation powder of PLGA/Chitosan/PVP was spread on the middle of filter paper to form a layer of dry powder. Slowly from one corner, water was applied to filter paper until the filter paper and powder bed became completely wet. The filter paper was allowed to dry completely and observed for its film forming ability. The formulation formed a good film after wetting and remained adhered to the filter paper.

Adhesion Test 2:
A formulation of particles made from PLGA/Alginate were sprayed over a piece of wet meat.
The particle swelled and formed a good film over the surface of the meat with excellent adhesion
The film could not be washed off by water.

Example 4

Manufacture of Exemplary Formulations

Manufacture of PLGA/Chitosan/PVP Formulation (35:50:15)

1. Preparation of PLGA solution: An amount of acetone (350 mL) was transferred to a clean glass beaker. PLGA (3.5 g) was slowly transferred to acetone in beaker while stirring. Mixture in beaker was vigorously stirred and mixed using magnetic stirrer until clear 1% solution was formed.

2. Preparation of Chitosan solution: An amount of deionized (DI) water (490 mL) was transferred to another clean glass beaker. Acetic acid (10 mL) was added to water in a beaker and mixed well to make a 2% acetic acid solution in water. Chitosan (1 g) was slowly added to the solution and the solution was mixed. The mixing speed was increased and continued until a clear solution was formed.

3. Preparation of PVP solution: An amount of DI water (150 mL) was transferred to another clean beaker. An amount of PVP (0.3 g) was added to the water with mixing on another magnetic stirrer. The mixing was continued until a clear 0.2% solution was formed.

4. Preparation of formulation: Five parts of Chitosan solution (500 mL) and 1.5 parts of PVP solution (150 mL) were mixed well in another clean beaker and mixing was continued to form a uniform solution.

5. The Chitosan-PVP solution was then slowly added to 3.5 parts of PLGA solution (350 mL) with vigorously stirred with a magnetic stirrer. Upon slow continuous addition, the solution started to form a white milky solution or suspension.

6. The stirring of the formed milky solution was continued with the magnetic stirrer for about 16-18 hours in a hood to evaporate acetone from formulation solution.

7. Spray Drying: The formulation solution was then transferred to a Yamato spray dryer to spray the formulation and form the formulation microparticles.

8. Before spraying the formulation solution, the spray dryer was allowed to equilibrate by running it with DI water spray for at least 15-20 min with set parameters.

9. Once the spray dryer attained equilibrium with set parameters (e.g., inlet temperature, drying air and atomizer temperature) the formulation was fed to the spray dryer and continuously observed. The formulation solution was continuously stirred on a magnetic stirrer during spray drying process. All observable spray drying parameters (e.g., outlet temperature, actual set temperature, solution flow arte, gas pressure, spray nozzle size, etc.) were monitored and recorded.

10. Once the spray drying of the formulation spray was completed, the spray dryer continued to run with DI water for at least 5 min and slowly turned off to cool down by switching off the temperature, drying air flow, and atomizer knobs.

11. The formulation collection bottle was slowly unscrewed form the unit and secured properly.

Example 5

Acute and Chronic Animal Studies

Acute and chronic studies of the performance of adhesion barriers were studied. These studies were performed on adult dogs, pigs, and sheep. In these studies a surgical incision was made in the thorax of the studied animal and lung and heart were exposed. Formulations were deposited on the exposed surface of the organ using a pressurized suspension of the particles in HFA propellant.

In the acute studies, the particles were applied and the condition of the film formed from the particles was observed. In the chronic studies, the condition of the film was observed up to 23 days.

TABLE 3

Summary of Acute and Chronic animal studies.

| | Formulation (% is wt %) | Acute Results | Chronic Results (after 23 days) |
|---|---|---|---|
| 1 | 70/30 PLGA/PVA 80%/20% | Formed good film with consistent spray | — |
| 2 | Chitosan/PVA 80%/20% | Formed excellent film immediately with consistent spray | Formed excellent film immediately with consistent spray. No adhesion was observed, but some red cells. |
| 3 | Chitosan/PVP/PLGA 30%/15%/55% | Formed good film with consistent spray | — |
| 4 | Chitosan/PVP/PLGA 50%/15%/35% | Formed excellent film immediately with consistent spray | Formed excellent film immediately with consistent spray No adhesion was observed after 3 weeks implant. Partial degradation with some material remaining |

FIG. 10 depicts a photograph of chronic sheep preparation at the time of implant. Formulation #2 and formulation #4 were sprayed over different lung areas and heart areas for the formulation evaluation. A section without particles sprayed was used as control. The formulations can been seen as they where initially applied to the sheep lung and heart.

FIG. 11 depicts a photograph of a chronic sheep implant at the time of reexploration, 23 days after the initial implant. The photograph demonstrates the development of the biodegradable film/barrier on the sheep lung. No adhesion of tissue on either side of the film/barrier was observed.

FIG. 12 depicts a photograph of a chronic sheep implant at the time of reexploration, 23 days after the initial implant. The photograph demonstrates the development of the biodegradable film/barrier over the sheep heart (left atrial appendage) and lung (the top portion of the photograph), and the lack of adhesion formation on both sides of the biodegradable film/barrier (between the heart and the barrier, and between the film/barrier and the lung).

FIG. 13 depicts a photograph from the same preparation as in FIG. 12 showing another view of the biodegradable film/barrier over the heart (left atrial appendage), which clearly demonstrates lack of adhesions and the development of a safe and easy to dissect film/barrier over the heart (left atrial appendage).

FIG. 14 depicts a photograph of a chronic sheep implant at the time of reexploration, 23 days after the initial implant. The photograph clearly demonstrates how the formulation has formed a film/barrier between the sheep lung (visceral pleura) and the chest wall (parietal pleura).

FIG. 15 depicts a photograph from the of chronic sheep implant in FIG. 14, demonstrating the development of the biodegradable film/barrier which functioned as the adhesion barrier described in FIG. 14.

FIG. 16 depicts a photograph of histologic results of the biodegradable film/barrier depicted in FIG. 15. The histology shows a clear delineation between the lung (visceral pleura), the barrier (Test Article), and the perietal pleura (pleura). The biodegradable film/barrier (Test Article) creates a barrier by forming a typical foreign body reaction (reactive fibrosis) resulting in a capsule or pseudo-membrane around the biodegradable film/barrier.

Example 6A-C

Particle Size Control in Spray Drying

Example 6A

Effect of Atomization Air Pressure on Particle Size

80% Chitosan/20% PVP Formulation

As the atomization air pressure changed from 0.15 to 0.1 MPa, the particle size changed from 6 and 85 microns.

Example 6B

Effect of Molar Composition of Polymers on Particle Size

TABLE 6

Particle size of PLGA/Chitosan/PVP formulation

| Molar | Particles size (microns) |
|---|---|
| 60/30/10 | 50 |
| 35/50/15 | 14 |

Example 6C

Adding Surfactant Mannitol

A surfactant was added to a PLGA/Alginate formulation prior to spray drying. Without surfactant, the particle size was 12 microns and with the surfactant the particle size was 76 microns.

What is claimed is:

1. An adhesion barrier, which is a biodegradable film formed from a formulation consisting essentially of:
   a plurality of dry particles consisting essentially of a polymer combination, wherein
      the polymer combination consists essentially of at least one biodegradable polymer selected from the group consisting of 50/50 PLGA and 70/30 PLGA and at least one water soluble polymer selected from the group consisting of PEG, PEG block copolymers, sucrose, starch, alginate, PVP, chitosan, PVA and any combination thereof, wherein
      the formulation is capable of absorbing moisture from a tissue to which it is applied thus forming, by swelling and overlapping of the particles, a film that reduces adhesion of the tissue surface to other body tissue(s).

2. The formulation of claim 1, wherein a mean size of the plurality of particles is between 700 nm and 200 microns.

3. The formulation of claim 1, wherein the plurality of particles is uniformly suspended in a liquid, wherein the liquid has a boiling point below 0° C.

4. The formulation of claim 1, wherein the polymer combination is selected from the group consisting of 70/30 PLGA and PVA; chitosan and PVA; and chitosan, PVP, and PLGA.

5. The formulation of claim 1, wherein the plurality of particles further comprise a therapeutic agent selected from the group consisting of an anti-inflammatory, anti-infective, hemostatic, chemotherapeutic, and any combination thereof.

6. The formulation of claim 1, wherein the film loses strength at a time between 30-60 days after the absorption of the moisture.

* * * * *